United States Patent [19]

Smith et al.

[11] 4,285,241

[45] Aug. 25, 1981

[54] METHOD AND APPARATUS FOR THE DETERMINATION OF THE MASS OF AN IMPACTING OBJECT

[75] Inventors: John R. Smith, Monroeville; William Ciaramitaro, Murrysville; Raj Gopal, Pittsburgh, all of Pa.

[73] Assignee: Westinghouse Electric Corp., Pittsburgh, Pa.

[21] Appl. No.: 57,524

[22] Filed: Jul. 13, 1979

[51] Int. Cl.³ .................. G01H 13/00; G01M 7/00
[52] U.S. Cl. .......................... 73/572; 73/579; 73/659
[58] Field of Search .............. 73/572, 579, 658, 659; 340/683

[56] References Cited

U.S. PATENT DOCUMENTS

| | | |
|---|---|---|
| 3,554,012 | 1/1971 | Schoel . |
| 3,860,481 | 1/1975 | Gopal . |
| 3,901,090 | 8/1975 | Akey et al. ............... 73/572 |
| 4,184,205 | 1/1980 | Morrow ................. 340/683 |

*Primary Examiner*—S. Clement Swisher
*Attorney, Agent, or Firm*—C. M. Lorin

[57] ABSTRACT

The impact signal derived from an acoustic transducer has a unique signature represented by its frequency spectrum. The present invention generates under predetermined conditions with objects, each of definite weight and form, a series of impact signals for reference purposes and correlates an actual impact signal from an unknown impacting object with such reference impact signals by comparing the frequency spectra, thereby to indirectly recognize the impacting object.

6 Claims, 15 Drawing Figures

- ● ACCELEROMETER
- ▲ LOCATION OF SIMULATED IMPACTS
- ■ APPROXIMATE LOCATION OF INTERNAL IMPACT

MASS=2

FIG.11A.

MASS=4

FIG.11B.

MASS=6

METHOD AND APPARATUS FOR THE DETERMINATION OF THE MASS OF AN IMPACTING OBJECT

BACKGROUND OF THE INVENTION

The invention pertains to apparatus and method for the detection of an impact on a wall by objects such as projectiles, debris or loose parts in an environment surrounded by such wall, in general, and more particularly to the determination of the nature and/or number of impacts and/or the size of the impacting objects.

More specifically, the invention is applicable to metal impact monitoring on the wall of the pressurized water reactor vessel of a power generating station for providing improved detection and survey of the failure of primary system components in such stations. An early detection of component failures will prevent the occurrence of dangerous operating conditions such as could result from metal debris. Debris tend to concentrate in the steam generator inlet plenum and the bottom plenum of the reactor vessel. From such collecting points, the debris entrained by the primary coalant, will be projected by the stream against the walls defining the coolant paths of the primary system. For the detection of impacts, transducers are placed on the walls at locations where an early detection can most favorably be derived which is indicative component failure, in particular at the bottom of the vessel.

An essential condition with an acoustic transducer for such detection is to be able to discriminate against background noise and/or electric spikes in order to derive a true impact signal. This has been achieved in different ways. See for instance U.S. Pat. Nos. 3,554,012 and 3,860,481.

While one or more transducers in the monitoring system can detect the occurrence of an impact signal, it is desirable to know where the impact is, how many loose parts are impacting and of what size. In this regard, the impact signal may be affected by the force of the impact, the shape of the object, and more generally the way the wall is being hit by the object in motion, as well as by the distance of the point of impact from the transducer. While all these factors are important in "seeing" what happens behind the reactor vessel wall, past experience with a reactor is very small and merely accidental, so that the operator has practically no historical basis to infer from an actual impact signal what is occurring within the reactor.

An object of the present invention is to improve the capability of recognizing the seriousness of an impact inside a pressurized reactor vessel.

Another object of the invention is to provide a way of knowing from an actual impact signal derived with an acoustic transducer the size, nature and number of impacting objects behind a wall.

Experience has revealed that true impact signals derived from the opposite side of a wall monitored with acoustic transducers have a certain relation to the mass of the impacting object as well as the force of the impact, the velocity of the object, the size and the shape, and the hardness of the object.

Accordingly, a further object of the invention is to identify the mass, number and nature of impacting objects by establishing predetermined experimental conditions of impact providing well identified transducer signals as references to relate actual impact signals which are also transducer derived.

Still another object of the present invention is to recognize an impacting object from the primary spectrum of the impact signal monitored with a transducer.

SUMMARY OF THE INVENTION

Based on the notion that the impact signal derived from an acoustic transducer has a unique signature represented by its frequency spectrum, the present invention proposes to generate under predetermined conditions with objects, each of definite weight and form, a series of impact signals for reference purposes and to correlate an actual impact signal from an unknown impacting object with such referenced impact signals by comparing the frequency spectra, thereby to indirectly recognize the impacting object.

A set of reference data established in accordance with predetermined experimental conditions simulating possible impacts within a pressurized reactor vessel by objects having a mass within an expected mass range, are related to the frequency spectrum of actual impact signals derived from a system monitoring through acoustic transducers the occurrence of impacts inside the reactor vessel. The determination of the mass of an impacting object results from a correlation of the frequency spectrum of the impact signal with one of the frequency spectra, or predetermined data references, classified according to masses, whereby the mass of the impacting object is immediately known.

DESCRIPTION OF THE PREFERRED EMBODIMENT

Figure 1:
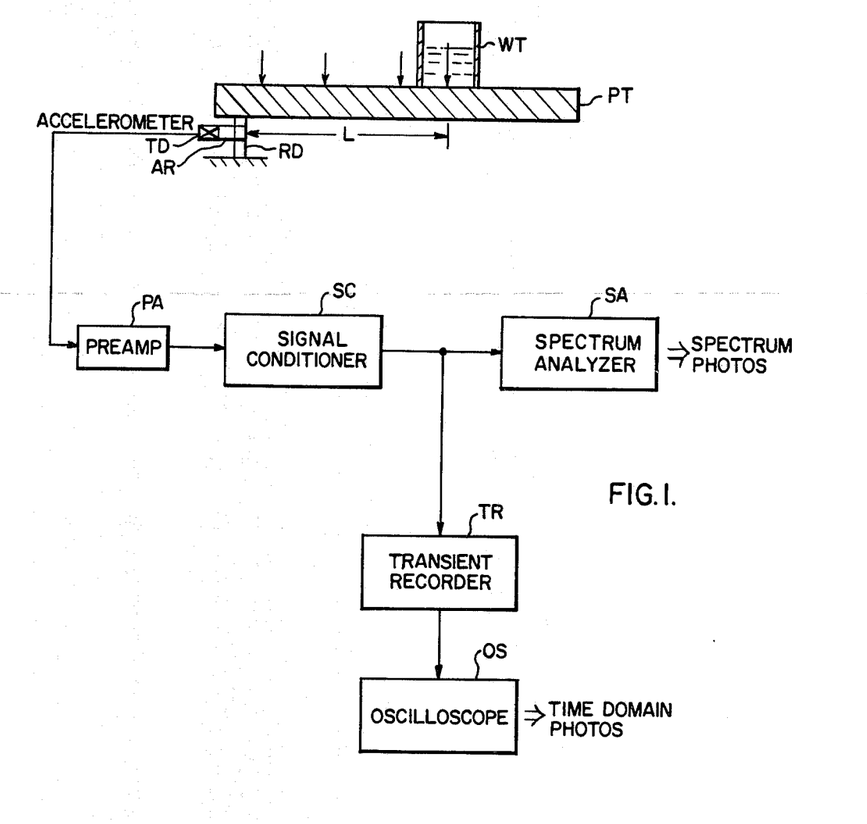
FIG. 1 schematically shows a plate test installation as can be used for simulating impact by dropping samples and for providing reference data in accordance with the present invention.
Figure 2A:
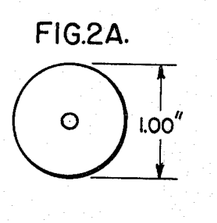
FIGS. 2A and 2B are side views of a stainless steel rod used as sample in the installation of FIG. 1.
Figure 2B:
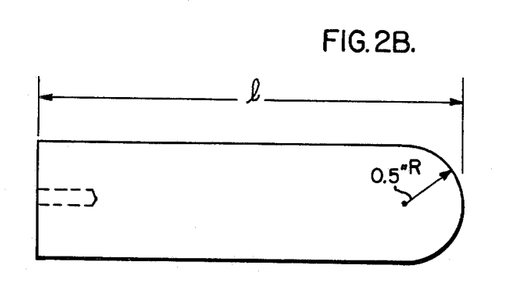

Referring to FIG. 1 an apparatus is schematically represented used for generating spectrum data under impact of samples such as generally shown in FIGS. 2A and 2B. A plate PT integral with a pipe RD to which is coupled a transducer TD by means of an arm AR, is used to receive impacts from objects falling at a distance $L_i$ from the sensing area defined by pipe RD. In order to approximate impact conditions in a reactor, a water tube WT is disposed in the zone of impact. FIGS. 2A and 2B typically show the form of an impacting sample. It consists in a stainless steel rod having a rounded end where it is to strike the surface of the plate.

As an illustration of the impact simulation experiment required in order to generate reference signals, in accordance with the present invention, plate PT is a rectangular steel plate of 213×368 cm. and 20 cm. thickness. Pipe RD has a 5 cm. diameter. It is tightly fitted against the bottom surface of the plate. The monitoring transducer TD is clamped to the pipe by the arm AR. Table I represents the lengths and weights of samples, like those shown in FIGS. 2A, 2B, used in the experiment.

TABLE I

| LENGTH (L) (IN.) | TOTAL WEIGHT (LB) |
|---|---|
| 13.65 | 3.0 |
| 11.40 | 2.5 |
| 9.16 | 2.0 |
| 6.91 | 1.5 |
| 4.66 | 1.0 |
| 2.41 | 0.5 |
| 1.19 | 0.25 |
| MATERIAL: 304 STAINLESS STEEL | |

The plate is struck by dropping various rods vertically, the hemispherical end down, onto the top surface of the plate from a height typically of 15 cm. The acceleration response is measured as shown in FIG. 1. A preamplifier connected with the output of the transducer provides a signal which, after passing through a signal conditioner circuit SC, is recorded in the time frame reference by transient recorder TC and displayed on an oscilloscope OS. The signal is also analyzed in the frequency frame reference by spectrum analyzer SA. Typically, the transient recorder is a Biomation 8100 device and the spectrum analyzer is a Nicolet 440 device. The transient recorder provides a display of the first 2 milliseconds of the derived impact signal. The spectrum analyzer provides the frequency signature. Typically, the spectrum lies in the range of 0 to 20 KHz and is based on the first 20 milliseconds of the impact signal. Table II, herebelow, shows data representative of the experiment. The distance $L_i$ from the zone of impact to the transducer area was chosen to be 90 cm.

TABLE II

| SAMPLES | | Frequency[b] | | | | |
|---|---|---|---|---|---|---|
| Wt. (lb.) | Rod Size (in.) | Band 1 0.2 kHz | Band 2 2–4 kHz | Band 3 4–6 kHz | Band 4 ~10 kHz | Band 5b,c ~20 kHz |
| 0.25 | 1.3 | 0.1(1)[c] | 0(0) | 0.8(8) | 0.4(4) | 0.8(8) |
| 0.5 | 2.4 | 0.2(1) | 0.1(0.5) | 0.9(4.5) | 0.3(1.5) | 0.3(1.5) |
| 1.0 | 4.7 | 0.6(1) | 0.2(0.33) | 1.4(2.3) | 0.3(0.5) | 0.3(0.5) |
| 2.0 | 9.2 | 0.9(1) | 0.3(0.33) | 1.0(1.1) | 0.2(0.22) | 0.5(0.55) |
| 3.0 | 13.6 | 1.5(1) | 0.4(0.27) | 0.8(0.53) | 0.4(0.27) | 0.5(0.33) |

Data normalized to Band 1 are shown in parentheses.

Figure 3:
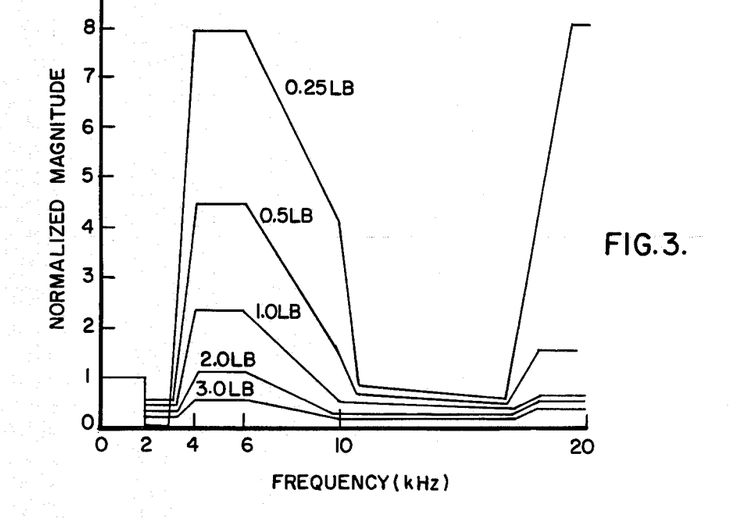
FIG. 3 shows normalized frequency spectra obtained for five typical samples like the one of FIGS. 2A, 2B.

FIG. 3 is a representation in the frequency domain of the results of Table II. This graph is normalized so that the 0–2 kHz portion of the spectrum has a magnitude of 1 for all impacts. As it appears from FIG. 3 the relative amount of low-frequency content in the signal increases with rod length and mass.

Having established reference data by dropping samples of definite shape, length and weight, the validity of the results, was thereafter confirmed by testing with bolts, nuts, ball bearings, wrenches and even a steam generator tube plug was used for more conformity with actual situations. These experiments were conducted for several drop heights, for different values of $L_i$, as well as for in-air versus in-water drops. These experiments revealed good similarity in the results. The inescapable conclusion was that the frequency spectrum constitutes a valid signature for impacting objects of a definite mass, whatever the shape, or size.

The preceding considerations were under the assumption of a perfect impact on the wall in relation to the particular transducer. Actually, wide variations were to be expected in the frequency data derived from plant operation. Indeed, many structures are obstructing the vessel bottom. Loose objects are most likely to collect and to hit the wall of such structures. Impacts on such different structures could result in different spectrum characteristics on account of the structure resonances. Moreover, most impacts, in general, would not be end-on, but rather they could occur at intermediary point along the body of the impacting loose part. Nevertheless, several criteria can be used to validate an impact as being against the vessel wall. At least some of the sensors will have a good reception of the signals, when several sensors are used at the bottom of the vessel. Also, the occurrence of short signal rise times and consistent signal arrival times at the several transducer locations is a strong indication of a valid information.

From the above considerations, impact spectra at the plant were obtained which reveal that there is a good similarity between actual impact spectra and those used as reference data and derived from impacting sample rods on a test plate.

Having put in evidence the validity of the mass signature of an object impacting the wall of a reactor vessel, it appears reasonable, according to the present invention, to gather reference data on a reactor vessel for ulterior use in the direction of actual impacts inside that particular reactor vessel. Because the same reactor structure is involved in simulation data collection and impact actual detection, and the same aggregation of transducers is used with the impact monitoring system, the simulation is closer to reality.

Figure 4:
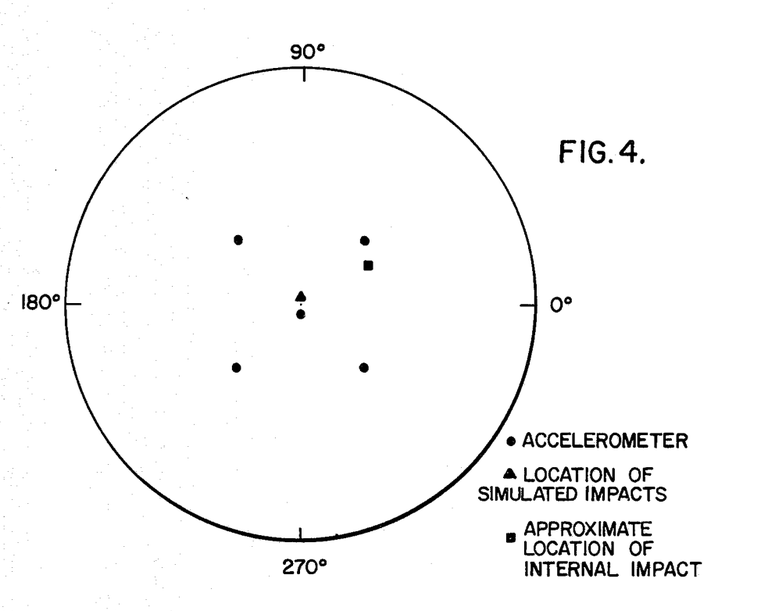
FIG. 4 shows the bottom of the vessel of a pressurized reactor with indication of (1) the locations of simulated impacts done by striking, with samples such as the one shown in FIGS. 2A and 2B, the outside of the wall vessel, (2) the location of an internal impact and (3) the location of acoustic transducers.

Impact simulation was performed by striking the outer surface of the vessel, near the bottom, with five of the same objects used in the laboratory, namely 0.25; 0.5; 1.0; 1.5 and 2.0 pound stainless steel rods, such as shown in FIGS. 2A, 2B. Data from the experiment were then compared to impact signals detected later which were due to internal impact. The verification was performed following an actual shutdown sequence of all the coolant pumps. It appeared from the signals received that the particular impact almost certainly was against the vessel wall. All the signals derived from the several transducers at the bottom of the vessel exhibited short rise times and reasonably high peaks. Moreover, the arrival time differences were consistent with a definite location in relation to the various transducers. FIG. 4 shows the bottom of the reactor vessel with a symbol indicating the bottom of the reactor vessel with a symbol indicating the locations of the accelerometers, the locations of simulated impacts done by striking the wall from the outside, and the assumed location of the above-mentioned internal impact. It is reasonable to assume that any response of the accelerometers to the external source of impact were the same as for a response to the internal source, as it is if it is with the same frequency range and distribution.

Measurements performed, with two accelerometers identified as channels 752 and 753, under simulation against the vessel wall with rods of respective masses 0.25; 0.5; 1.0; 1.5 and 2.0 are indicated herebelow.

TABLE III

| | Rod Mass (lb) | Amplitude at Indicated Frequency[a] | | |
|---|---|---|---|---|
| | | [2.86 kHz | 10.7 kHz | 15.7 kHz][b,c] |
| CHANNEL 752 | | | | |
| Background noise | 0.25 | 0.22 | 0.45 | |
| Sample | 0.25 | 0.9 | 0.6 | 0.7 |
| " | 1.0 | 2.6 | 0.65 | 1.0 |
| " | 1.5 | 3.8 | 0.33 | 0.9 |
| " | 2.0 | 4.8 | 0.45 | 1.2 |
| CHANNEL 753 | | | | |
| Background noise | 0.18 | 0.5 | 0.63 | |
| Sample | 0.25 | 0.7 | 0.5 | 0.56 |
| " | 0.5 | 1.6 | 0.47 | 0.88 |
| " | 1.0 | 2+ | 0.8 | 0.83 |
| " | 1.5 | 2++ | 0.55 | 0.8 |
| " | 2.0 | 5.1 | 0.6 | 1.6 |

[a]Data given in units of recorder scale

Table III shows for each source the relative magnitudes for the three respective frequency components of the impact signals. The selected frequencies represent sensor/structure resonances. The data indicate clearly that, as the size of the impact source increases, the relative amount of low frequency content in the signals also increases.

Table IV, herebelow, shows frequency components defining spectrum of the impact signal for the two reception channels 752, 753, as recorded in the case of the above-mentioned internal impact.

TABLE IV

| Channel | Level at Indicated Frequency | | |
|---|---|---|---|
| | [2.86 kHz | 10.7 kHz | 15.7 kHz][b,c] |
| 752 | 3.6 | 0.86 | 1.87 |
| 753 | 2.7 | 0.64 | 2.5 |

At the same time, time and frequency domain photographs were closely examined in order to estimate by comparison with the external impacts the size of the loose part. Also, the photos were qualitatively compared to simulation photos. The net result of such analysis was that the loose part size most likely was equivalent to the 0.5 pound (0.23 kg) steel rod.

From the above considerations it appears that a low-noise, wide-bandwidth monitoring system has been designed having the capability of directly locating a loose part and determining its mass. The monitoring system also offers a way of recognizing the movement of the loose part, as well as of detecting the number of loose parts behind the wall of a reactor vessel.

Figure 5:
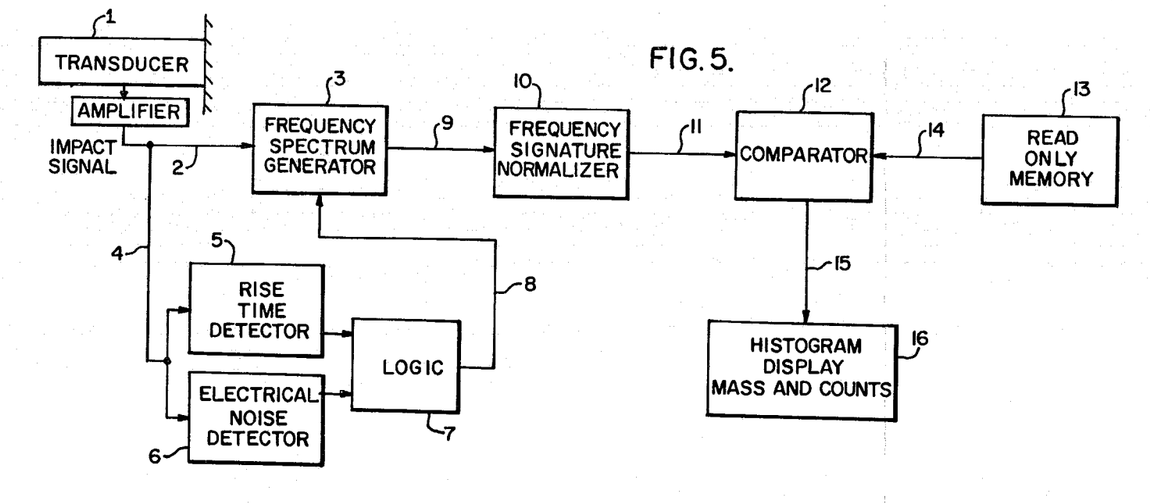
FIG. 5 is a block diagram illustrating the method according to the invention.

Referring to FIG. 5, a block diagram is shown that can be used for performing electrically a quantification of the mass for loose parts detected in the primary loop of a pressurized reactor vessel. The circuit of FIG. 5 effectuates the processing of the frequency signature of impact signals derived on line 2 from an acoustic transducer 1 placed against the wall of the vessel. The frequency signature of the impact signal is obtained by its frequency spectrum derived from frequency spectrum generator 3 whenever gated on line 8 by a circuit which ascertains that the signal on lines 2 and 4 is a true impact signal, thus, not a noise, or other irrelevant type of signal. The latter circuit includes a rise time detector 5 which determines whether on line 4 a derived signal has a sharp edge, and whether, by a second circuit 6, the signal is above a minimum level for a sufficient length of time thereby denoting a signal other than a noise. If these two conditions are established successively in time and within a period defined by a timer, logic circuit will generate on line 8 a logic state representing a yes for a true impact. As a result, the frequency spectrum generator will output a valid signature on line 9. Since the frequency spectrum corresponding to an impact signal is affected by the energy of the impact, it is desirable for the purpose of processing the signature any further, to normalize the levels of the various frequency bands so that a reference can be always at unity energy level. This is achieved by the frequency signature normalizer 10.

The circuit of FIG. 5 also contains a read-only memory (ROM) containing a series of frequency spectra which have been gathered for various masses in accordance with the procedure and tests explained heretofore by reference to FIGS. 1 to 4.

As stated in relation to FIGS. 1 to 4 and Tables I, II and III, reference data corresponding to three frequency bands (as illustratively chosen and shown, namely 2.86 kHz; 10.7 kHz and 15.7 kHz for each of the sampled masses, namely 0.25; 0.5; 1.0; 1.5 and 2.0 pounds) have been stored in the read-only memory 13 of FIG. 5.

Figures 6A, 6B, 11A:
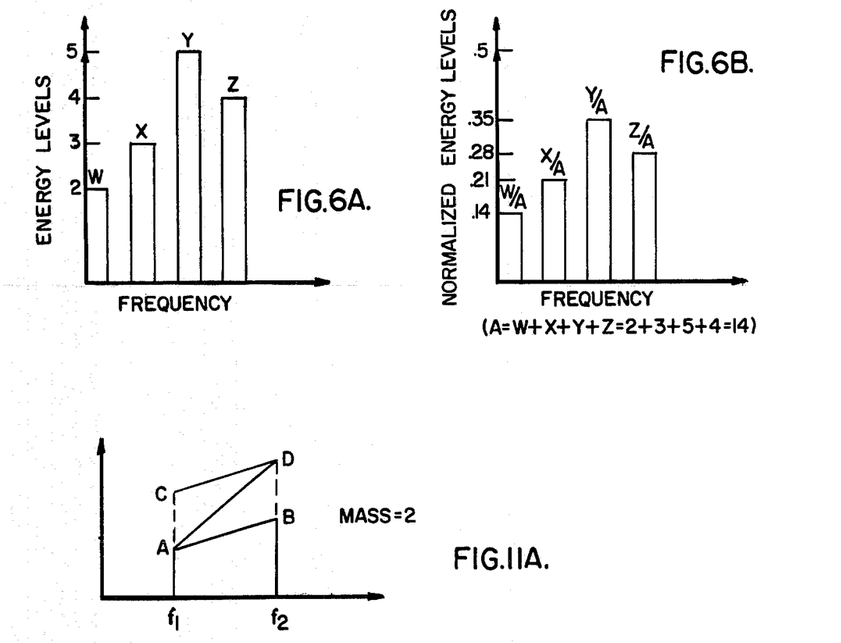
FIGS. 6A and 6B illustrate frequency spectra of an actual impact before and after normalization.
FIGS. 11A, 11B, 11C show valid signatures as received and compared in the PROM device of FIG. 10.

Referring to FIG. 6A, for the purpose of illustration four amplitudes W, X, Y, Z of a frequency spectrum signal are shown as would be obtained from an impact signal for a given sample e.g. mass. In order to normalize this set of four magnitudes for the purpose of comparison, referring to FIG. 6B, if $A=W+X+Y+Z$, each amplitude is reduced to a fraction having A as common denominator. Four binary coded values are stored in the read-only memory representing W/A, X/A, Y/A, Z/A, for each of the sample values, or masses. By associating in comparator 12 one of such referenced masses to the particular combination of four normalized amplitudes such as represented by FIG. 6B and as derived on line 11, e.g. the normalized signature of the impact signal of line 2, the mass of the impacting object is identified on line 15. Thus, comparator 12 recognizes which of the combinations on line 14 matches exactly the combination on line 11. When this is done, on line 15 the corresponding mass is directly obtained for display at 26. In other words, the mass information is obtained by processing the frequency signature of the received time history acceleration impact data. The impact signal is converted from a time domain into a frequency domain. The normalized frequency signature data is compared with reference data from the read-only memory (ROM) which has stored mass information associated with the various frequency bands or discrete frequencies. The mass determination unit sequentially reads the memory data and computes a performance index. One example of such computation is:

$$J=(X_{ref}-X_{nor})^2+(Y_{ref}-Y_{nor})^3+(Z_{ref}-Z_{nor})^2$$

where $X_{ref}$, $Y_{ref}$, and $Z_{ref}$ are reference frequency component amplitudes from the ROM, and $X_{nor}$, $Y_{nor}$, and $Z_{nor}$ are normalized frequency component amplitudes of the incoming impact signal. The minimum value of the performance index is determined. The mass associated with the reference data yielding the minimum value of the performance index appears on the histogram display. The display provides information on the number of impact signals processed versus the mass estimates. This allows the most probable estimate of the loose part mass to be determined. The impact acceleration time history signal of line 2, which is caused by an impacting loose part, is inputted into frequency spectrum generator 3 and the associated two detectors 5, 6. The latter provides a logic signal indicating whether to accept or reject the incoming signals. In order to be valid, the incoming signal must meet two criteria: (1) have a sharp rise time indicative of impacts on the pressure boundary surface near the transducer detecting the loose parts, and (2) have sufficient decay time indicative of a loose part, not of an electrical transient. This is accomplished by ANDing the outputs of the rise time discriminator 5 and of the electrical noise discriminator 6. Once the signal is accepted as valid, the frequency signature generator is gated to output the necessary signal data on line 9. The time domain signal is converted into the frequency domain. Signal processing may be accomplished with a frequency spectrum analyzer, analog, or digital, bandpass filters, or a computer treating data according to a fast fourier transform program. For the purpose of comparing two signatures, the frequency signature from generators 3 may be normalized by finding the ratios of various frequency bands and discrete frequencies to a reference frequency band and the normalized frequency signature is stored into the comparator mass determination unit. Another way of normalizing the signal is as shown in FIG. 6B, by taking the sum A of the outputted levels and using A as common denominator 12 to obtain individual fractions. The reference frequency, or associated mass information, from the read-only-memory (ROM) 13 is compared with the normalized frequency data in the mass determination unit by calculating an index of performance. As earlier stated, an example of such a calculation is:

$$J = (X_{ref} - X_{nor})^2 + (Y_{ref} - Y_{nor})^2 + (Z_{ref} - Z_{nor})^2 \text{ ps}$$

where $X_{ref}$, $Y_{ref}$, and $Z_{ref}$ are from the ROM and $X_{nor}$, $Y_{nor}$ and $Z_{nor}$, are normalized input frequency bands or discrete frequencies. When the value of the performance index reaches a minimum the mass value associated with $X_{ref}$, $Y_{ref}$, and $Z_{ref}$ is displayed and ascertained with the histogram display unit. The sequence of impact data is allowed to continue until time has elapsed which is sufficient for a reliable mass determination of the loose part. The display unit may consist of a series of LED indicators, and the printout may come from a chart recorder.

Figure 7:
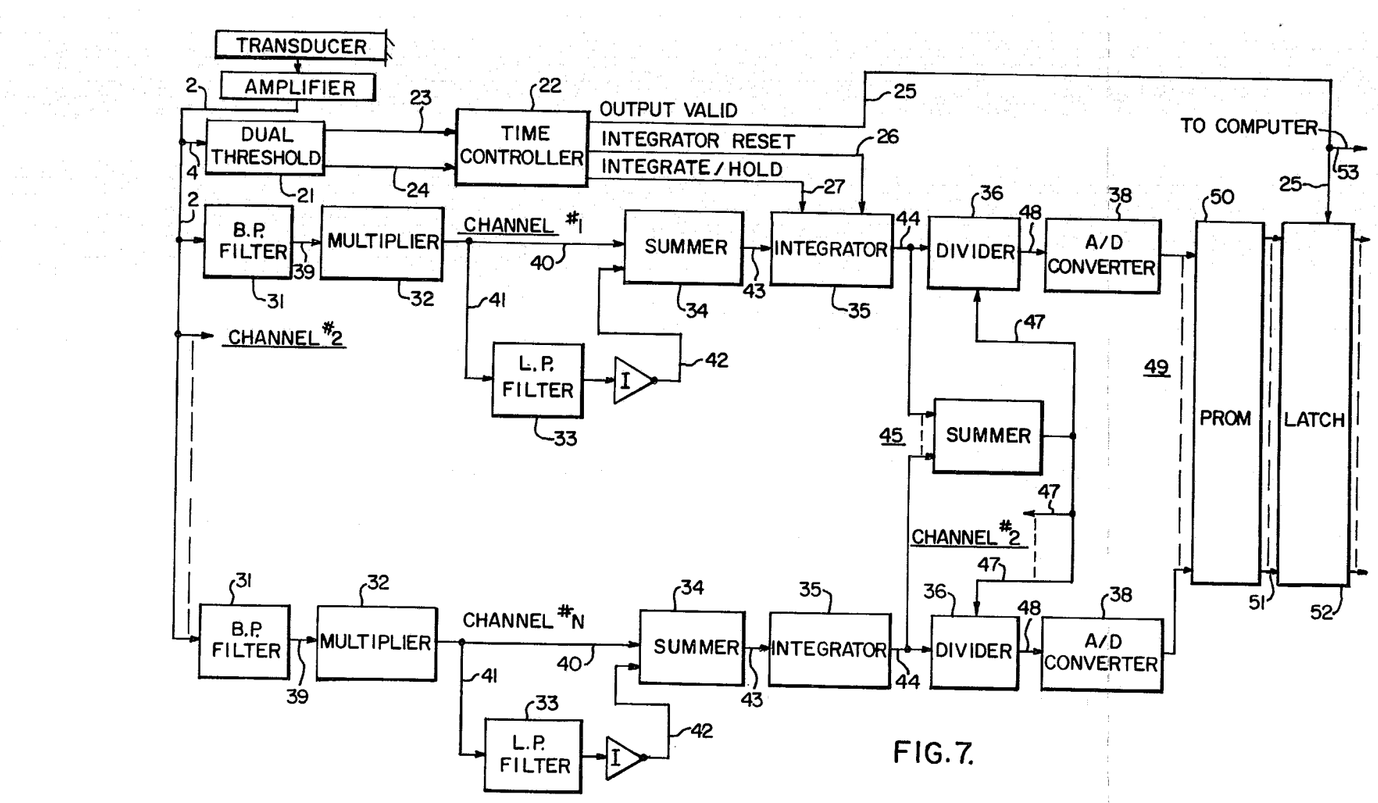
FIG. 7 is a schematic representation of the overall circuitry of the impact monitoring system according to the present invention.

Referring to FIG. 7, an actual implementation of the diagram of FIG. 5 is shown to include N frequency band channels individually controlled by a time controller 22 associated with a dual threshold detector 21. All channels concur in providing on parallel lines 49 binary inputs like the one on line 11 of FIG. 5, which represent N discrete amplitudes in binary form used as input addresses from a PROM device 50 combining the functions of blocks 12 and 13 of FIG. 5. All frequency channels are like the channels 1 and N shown in FIG. 7. The dual threshold detector 21 and the time controller 22 of these channels appear in detail on FIG. 8. FIG. 9 provides a number of curves explaining the timing of operation of circuit elements found in FIGS. 7 and 8.

Figure 10:
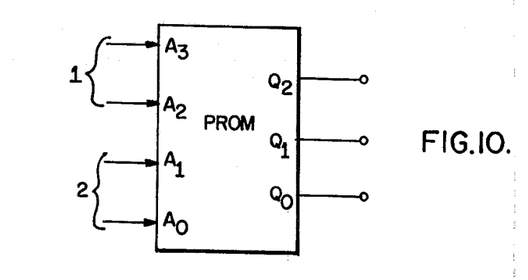
FIG. 10 is a block representation of the PROM device of FIG. 7 in an illustrative situation.

Considering again FIG. 7, transducer $T_1$, attached to the wall of the pressurized reactor (preferably at the bottom), responds to all kinds of vibrations as well as to any acoustic propagation occurring through the wall, in particular, one due to an impact. Accordingly, on line 2, transducer $T_1$ outputs continuously signals which may be mere background noise, but also an actual impact. Curve (a) of FIG. 9 shows in simplified form a continuous signal as typically would appear on line 2. From A to B and from C to D the signal segments are noise at different levels, with occasionally a spike at E, whereas from B to C the signal presents a unitary characteristic exhibiting successive peaks and of an overall duration. These are the features which the dual threshold detector 21 and the time controller 22 contribute to recognize, thereby to allow by line 25 latching at 52 of data derived from PROM device 50. Curve (b) of FIG. 9 represents in simplified from a true impact signal, e.g., similar to signal segment BC of curve (a). The signal derived on line 2 is supplied in parallel to N channels having respective band-pass filters 31 each selected to match an intended frequency of the spectrum. Thus channels 1 to N could be like bands 1 to 5 in aforementioned Table II. Following the pass-band filter, the signled-out signal on line 39 is squared by a multiplier 32 in order to provide an energy indicative signal for the particular frequency, thus equivalent to W, X, Y or Z in FIG. 6A. The energy signal on line 40 is applied to one input of a summer 34, while by line 41 the low frequency portion e.g., the noise background of the signal of curve (a), is being extracted via low-pass filter 33. After inversion by inverter I, the derived signal is subtracted from the signal of line 40 by means of summer 34. Therefore, at the output and on line 43, the impact signal has become free from background component. Integrator 35, gated by line 27 and reset by line 26 from the time controller, provides on line 44 the equivalent of W, X, Y, or Z of FIG. 6A. Via lines 45, in every channel, the signal of line 44 is inputted into a summer 46 in order to generate the equivalent of $W + X + Y + Z = A$ of FIG. 6A. The output 47 is combined with the signal of line 44, in each channel, by divider 36, to provide the equivalent of W/A, X/A, Y/A, or Z/A of FIG. 6B, e.g., the normalized frequency amplitudes. For illustration purpose, in FIG. 6A, $W = 2$; $X = 3$; $Y = 5$ and $Z = 4$, thus, $A = 14$. The normalized frequency amplitudes generated by divider 36 appear on line 48. A/D converter 38 converts such analog amplitude into a digital signal of so many bits on lines 49 which are inputted into PROM device 50. The output of the PROM on line 51 is a digital representation of the value of the mass corresponding to the particular input combination, e.g., the discrete series of magnitudes characterizing the spectrum signal, on lines 49. If the signal of line 2 is a true impact, a gating signal on line 25 recognizing a valid output causes the latch device 52 to latch the output data of line 51. At the same time by line 53 a computer (not shown) is informed that new valid data in association with transducer $T_1$ are being available for digital treatment, for instance for logging, alarm, hyperbolic triangulation, etc...

the operation of PROM device 50 will now be explained with an example as follows:

For the sake of simplicity, it is assumed that only two channels are necessary in order to derive a valid signature of the impact signal of line 2. Then, on FIG. 7, $N = 2$, and there exists only two channels corresponding to two frequency bands $f_1$ and $f_2$. It is also assumed that 2 binary bits are used per channel in order to indicate the level (X, or Y) signal. In addition, three output bits are assumed to be used for PROM 52, e.g., for lines 51 of FIG. 7, in order to represent the mass value resulting from the identification of the stored data reference with the impact signal. Accordingly, PROM 52 has inputs $A_3$, $A_2$ for frequency $f_1$ and inputs $A_1$, $A_0$ for frequency $f_2$, while $Q_0$–$Q_2$ are the outputs of the PROM, as shown in FIG. 10.

It is further assumed that the reference data stored in the PROM are according to the following table:

| $\left(\dfrac{X}{A}\right)$ for $f_1$ | $\left(\dfrac{Y}{A}\right)$ for $f_2$ | Mass |
|---|---|---|
| 1/4 | 3/4 | 2 lbs. |
| 2/4 | 2/4 | 4 lbs. |
| 3/4 | 1/4 | 6 lbs. |

Thus, for a mass of 2 pounds experiment has shown that the impact signature combines $X/A = \frac{1}{4}$ with $Y/A = \frac{3}{4}$; whereas $X/A = 2/4$ and $Y/A = 2/4$ correspond to a mass of 4 pounds and $X/A = \frac{3}{4}$, $Y/A = \frac{1}{4}$ represents a mass of 6 pounds.

From all the combinations possible on lines 49 for inputs $A_0$–$A_3$, namely 16, certain will match the overall picture of one sample signature, some will be relatively close, others will not at all be representative. The following is a valid table of truth for the stored data in PROM 50, e.g., of the relation between the inputs $A_0$–$A_3$ and the outputs $Q_0$–$Q_2$.

| Program | | |
|---|---|---|
| $f_1$ | $f_2$ | Output |
| 00 | 00 | 0 |
| 00 | 01 | 0 |
| 00 | 10 | 0 |
| 00 | 11 | 0 |
| 01 | 00 | 0 |
| 01 | 01 | 4 |
| 01 | 10 | 2 |
| 01 | 11 | 2 |
| 10 | 00 | 0 |
| 10 | 01 | 6 |
| 10 | 10 | 4 |
| 10 | 11 | 2 |
| 11 | 00 | 0 |
| 11 | 01 | 6 |
| 11 | 10 | 6 |
| 11 | 11 | 0 |

Figure 11B:
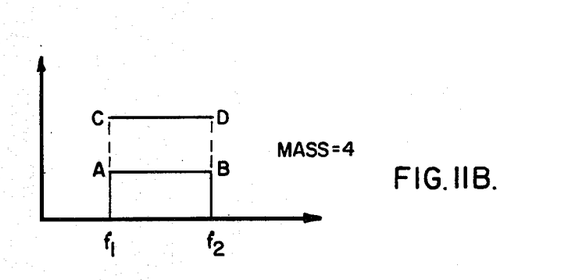
Figure 11C:
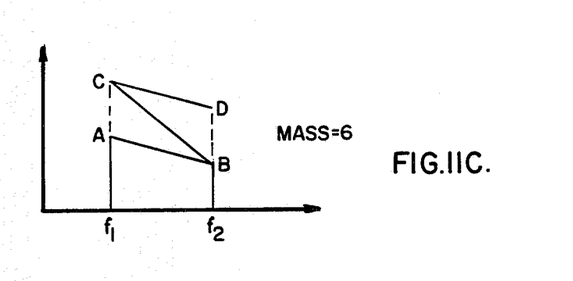

Referring to FIGS. 11A, 11B, 11C, the table of truth establishes the identity, or at least a cose similarity between the referred mass and an input combination ($A_0$–$A_3$).

Thus, for the mass of 2 pounds, AB, AD, and CD are considered comparable in representing the relative levels ($\frac{1}{4}$, $\frac{3}{4}$) of the two bands ($f_1$, $f_2$), as it appears from lines 7, 8 and 12 of the table of truth. For a mass of 4 pounds, the levels are equal (2/4, 2/4) and the level of AB and CD are found to be close enough to be both representative, whereas, for a mass of 6 pounds (higher level on low frequencies), lines 10, 14 and 15 would be considered comparable signatures. All other possible combinations have been given a zero value (0) so as to indicate that no "valid" mass has been detected. This is the case, for instance, of all combinations denoting zero level on one of the frequency bands. This is also the case of line 16, since a maximum level (11) is not indicative of the situation shown by FIG. 11B (too high a magnitude, just like line 1 was too low for both frequency bands in the other extreme situation).

Figure 8:
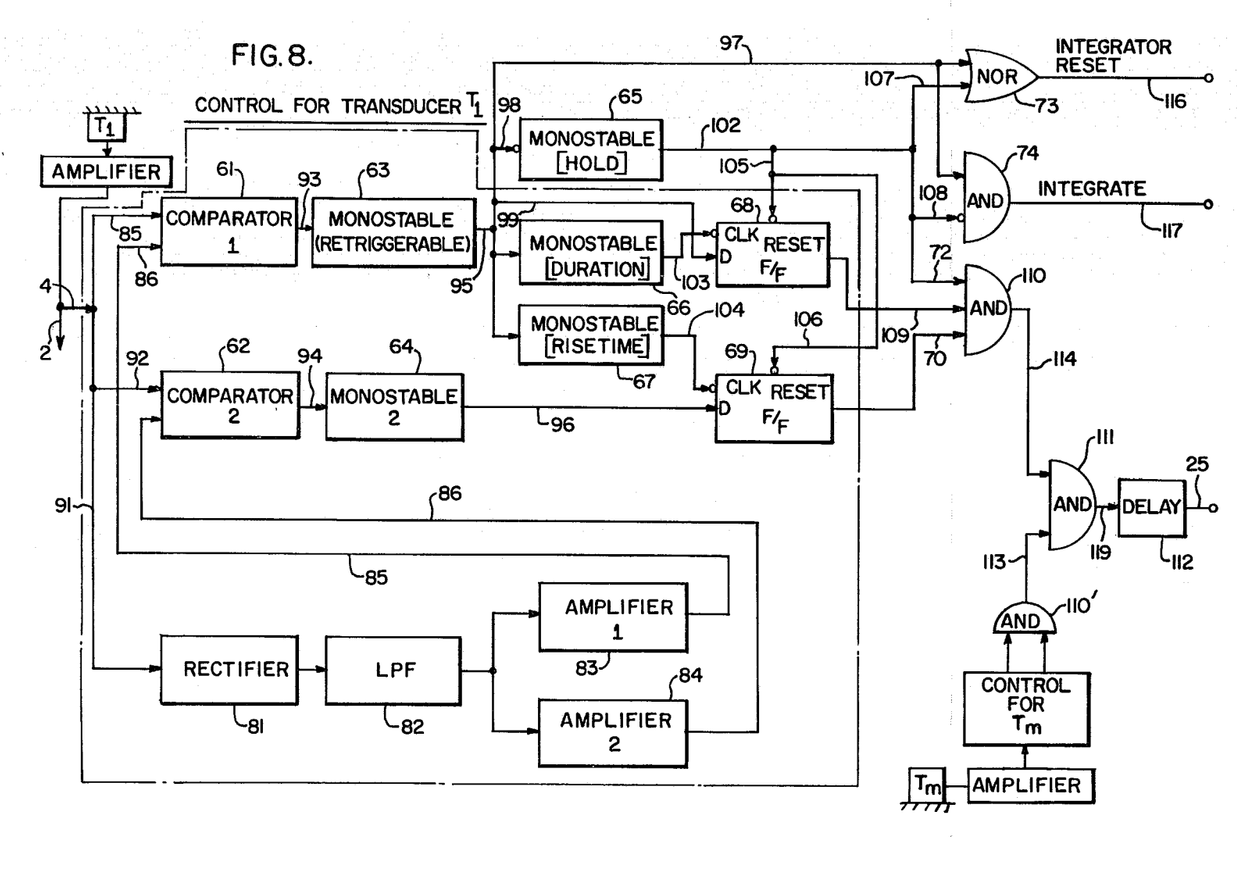
FIG. 8 is a detailed view of the timer circuit which is part of the circuit of FIG. 7.
Figure 9:
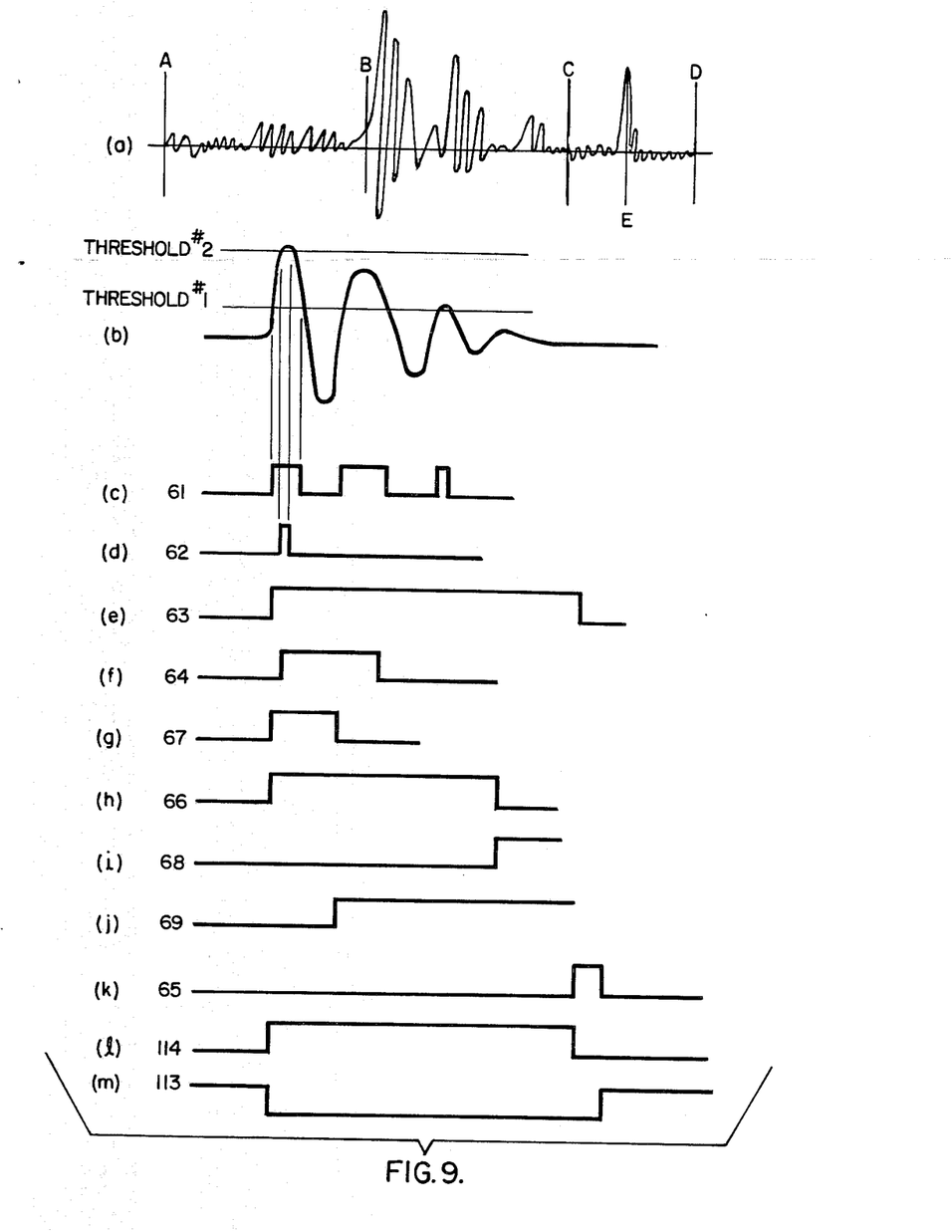
FIG. 9 shows with curves the operation of the circuit of FIGS. 7 and 8.

Referring to FIG. 8, the combined functions of the dual threshold detector 21 and time controller 22 of FIG. 7 will now be considered by reference to the curves of FIG. 9 where curve (a) is typical of an actual signal of FIG. 9 where curve (a) is typical of an actual signal continuously received on line 4 from a transducer and curve (b) is typical of an impact signal free from background noise. The dual threshold detector includes a comparator 61 for a first threshold and a comparator 62 for a second threshold. The first and second thresholds are shown on curve (b) of FIG. 9. The first threshold intersects three peaks of the impact signal curve, while the second and higher threshold intersects only the highest and first peak. Monostable vibrators 63 and 64 are associated with the outputs on respective lines 93 and 94 of the respective comparators 61, 62. As shown by curves (c) and (d), crossing-over points are detected by the respective comparators 61, 62 and pulses are generated on the respective lines 93, 94, three pulses for curve (c) and one pulse for curve (d). Monostable vibrator 63 is retriggerable, so that, before the occurrence of the trailing edge of a constant pulse generated on line 95, the outputted pulse is lengthened twice before its timely expiration. The total pulse outputted on line 95 is as shown by curve (e). Curve (f) shows the pulse triggered by the pulse of curve (d) with its trailing edge defined by the time constant of circuit 64. In order to identify a time impact signal, the fast rise time of the first peak and the duration of the overall succession of peaks have to be measured. Monostable vibrator 66 at the output of circuit 63 generates the signal shown by curve (h), which establishes a minimum duration. Flip-flop 68 receives at its data input by line 99 the indication that curve (e) is high for the time chosen. Flip-flop 68 is clocked by the signal of circuit 66, namely, via line 103. As a result, and as shown by curve (i), flip-flop 68 is set thereby recognizing that when circuit 66 goes low the retriggered circuit 63 is still high, e.g., the impact signal is still lasting. The output of flip-flop 68 when set presents on line 104 to AND device 110 the logic yes. Another flip-flop 69 is used to identify the fast rise condition. To this effect, the output on line 96 from the second threshold monostability vibrator 64 (curve f) is applied to the data input of flip-flop 69. Concurrently, the output on lines 95 and 101 from the first threshold monostable vibrator 63 is applied to a short time monostable vibrator 67 thereby generating curve (g) which is used to clock flip flop 69. As a result, and as shown by curve (j), flip-flop 69 is set and the logic yes is applied on line 70 to AND device 110 to indicate that the fast rise condition has been fulfilled. A monostable vibrator 65 responsive by lines 95, 98 to the inverse of the output of circuit 63 introduces the hold time of curve (k) following the fall of the pulse of curve (e). At the same time, the hold time of circuit 65 is applied via line 72 to AND device 110. Therefore, on line 114 the hold signal and the two set flip-flops establish on AND device 110 that a valid impact signal has just been received and has completed its expected minimum duration.

The outputs of circuit 63 and 65 are used as inputs to NOR device 73 in order to reset the integrators 35 via lines 26 for the various channels (FIG. 7). The fall of the monostable 65 pulse by lines 105 and 106 also reset the two flip-flops.

AND device 74 responds to the start of the pulse of circuit 63 (curve e) after the hold time of circuit 65 has occurred in order by line 117 and 27 to start integrating any signal coming on line 2 for each channel of FIG. 7.

As shown in FIG. 8 line 114 from AND device 110 indicates that a valid impact signal has been received by transducer $T_1$, when the two flip flops 68, 69 have raised the level of lines 109 and 70. This logic conclusion is combined with similar AND devices associated with other pairs of flip-flops for another transducer such as $T_m$ on FIG. 8. The valid signal at 113 is combined with the valid signal at 114 to control an AND device 111. As a result, an impact condition is recognized as valid on line 119 for the two transducers $T_1$ and $T_m$. Similarly the responses of several transducers can be compared in order to a ascertain whether all have responded to a true impact. If this is the case, after a delay (112) a command signal on line 25 is generated by AND device 111 for latching the output data of PROM device 50 and for commanding computer treatment by line 53 (FIG. 7). It is noted that the hold condition developed from circuit 65 and applied as third input by line 72 to AND device 110, needs only be used in association with one AND device 110 of one transducer ($T_1$ in FIG. 8), since the valid condition is common to all transducers.

We claim:

1. A method of detecting the mass of an impacting object behind a wall comprising the steps of: deriving an electric signal representative of an acoustic signal generated by the impact of said object; converting said electric signal into a frequency spectrum signal; comparing said frequency spectrum signal with a set of reference data each having a frequency spectrum indicative of the mass of an impacting sample for identifying matching with reference data from said set having the same relative importance in the spectrum; and providing an indication of the mass associated with such matching reference data which is indicative of the mass of said impacting object.

2. Apparatus for the detection of the mass of an impacting object behind a wall comprising:

acoustic means coupled with said wall for deriving at least one impact time signal representative of a true impact by said object;

means for converting said time signal into a frequency spectrum signal;

means for detecting similarity between said frequency spectrum signal and one of a plurality of spectrum reference data, with such similarity being the relative importance of the spectrum frequency components, said reference data being such associated with a definite mass of an impacting mass; and means for deriving an indication of mass associated with said one of said reference data of said set as representative of the actual mass of said impacting object.

3. The apparatus of claim 2 with said similarity detecting means: including programmable read-only-memory (PROM) means having digital input address terminals; digital output terminals; and switching means controlled by the address of said input address terminals for selectively switching with said output terminals predetermined logic states; said PROM means being programmed to establish a plurality of said predetermined logic states in accordance with reference data representing respective masses of imparting objects, whereby said output terminals provide a digital representation of mass corresponding to a digital address on said input address terminals.

4. The apparatus of claim 2 with said acoustic means constantly providing an oncoming signal when operative; with first threshold means responsive to said oncoming signal for detecting a fast rise amplitude of said oncoming signal as an indication of a time impact signal; with second threshold means for detecting a signal amplitude characteristic of minimum duration as an indication of a true impact signal; said converting means being operatively conditioned by concurrent detection by said first and second threshold means.

5. The apparatus of claim 2 with means interposed between said converting means and said similarity detecting means for changing said frequency spectrum signal into a normalized signal for the purpose of comparison with said spectrum reference data.

6. The apparatus of claim 5 with said normalized signal and said spectrum reference data being normalized to represent a combination of energy levels divided by a common denominator.

* * * * *